United States Patent [19]

Bazaral

[11] Patent Number: 4,925,448
[45] Date of Patent: May 15, 1990

[54] CATHETER PACKAGE

[75] Inventor: Michael G. Bazaral, Cleveland, Ohio

[73] Assignee: The Cleveland Clinic Foundation, Cleveland, Ohio

[21] Appl. No.: 176,227

[22] Filed: Mar. 30, 1988

[51] Int. Cl.$^5$ .............................................. A61M 5/00
[52] U.S. Cl. ..................................... 604/171; 206/364; 206/370
[58] Field of Search ................... 604/163, 171, 263; 206/363, 364, 370, 438, 439, 570, 571

[56] References Cited

U.S. PATENT DOCUMENTS

| | | |
|---|---|---|
| 3,166,189 | 1/1965 | Disston . |
| 3,633,758 | 1/1972 | Morse et al. . |
| 3,851,649 | 12/1974 | Villari . |
| 3,926,309 | 12/1975 | Center . |
| 3,934,721 | 1/1976 | Juster et al. ......................... 604/171 |
| 4,111,302 | 9/1978 | Roth ................................... 206/363 |
| 4,216,860 | 8/1980 | Heimann ............................ 206/370 |
| 4,262,800 | 4/1981 | Nethercutt ......................... 206/364 |
| 4,327,723 | 5/1982 | Frankhouser . |
| 4,351,333 | 9/1982 | Lazarus et al. . |
| 4,366,901 | 1/1983 | Short .................................. 206/364 |
| 4,405,047 | 9/1983 | Barba . |
| 4,515,592 | 5/1985 | Frankhouser . |
| 4,568,334 | 2/1986 | Lynn . |
| 4,634,433 | 1/1987 | Osborne ............................. 604/163 |
| 4,713,059 | 12/1987 | Bickelhaupt et al. ............... 604/171 |
| 4,721,123 | 1/1988 | Cosentino et al. .................. 604/171 |

OTHER PUBLICATIONS

Brochure of American Edwards Laboratories, American Hospital Supply Corporation regarding Swan-- Ganz Thermodilution Paceport Catheter and Chandler Transluminal V-Pacing Probe 472-9/86-cc, Copyright 1986.

*Primary Examiner*—Stephen C. Pellegrino
*Assistant Examiner*—Ralph Lewis
*Attorney, Agent, or Firm*—Fay, Sharpe, Beall, Fagan, Minnich & McKee

[57] ABSTRACT

A package for a catheter includes a main housing compartment for housing a distal section of an intravascular catheter. The main housing compartment has an opening allowing removal of the catheter therethrough and includes a first section for housing a distal end portion of the catheter which has at least one port. The first section further includes an absorbent member for absorbing a fluid flowing out through the catheter at least one port. The main housing compartment also includes a second section for housing the catheter central section and a sheath that is mounted thereon. The second section is located at a higher elevation than the first section to ensure that all of the fluid used to flush the catheter remains in the first section. A cover layer seals the main housing compartment from micro-organisms and particles in the surrounding environment but is removable to expose the catheter. A catheter proximal end holding section holds the proximal end of the catheter. An enclosing structure encloses both the main housing compartment and the catheter proximal end holding section to seal the catheter from micro-organisms and particles in the surrounding environment.

20 Claims, 4 Drawing Sheets

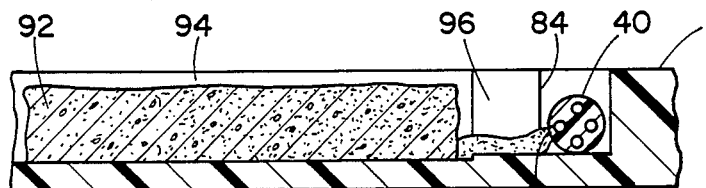
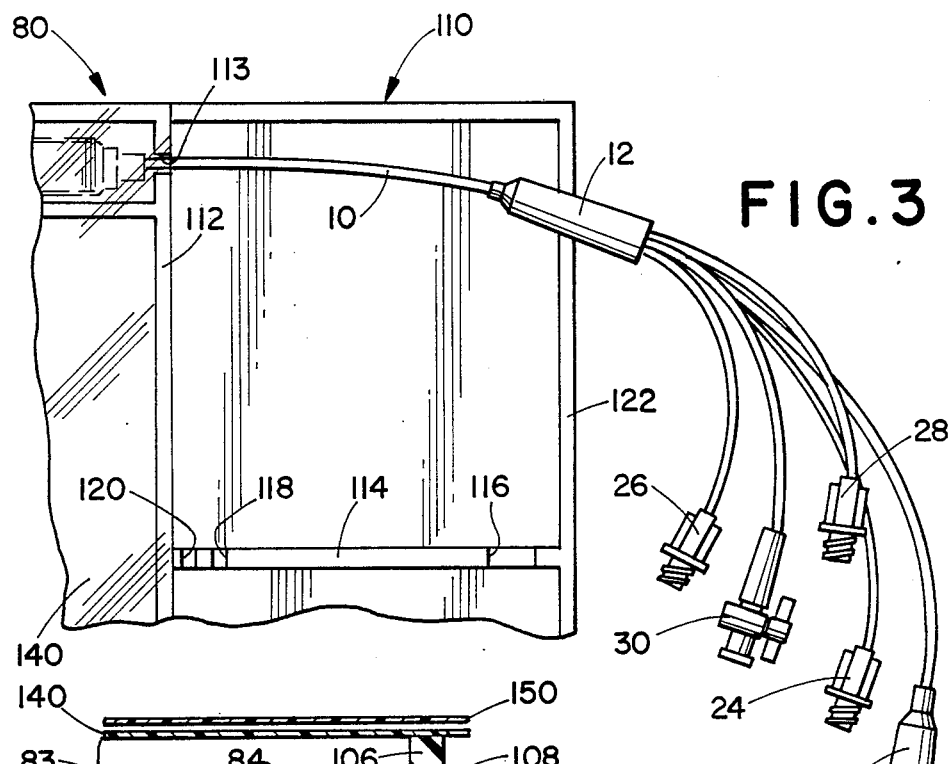
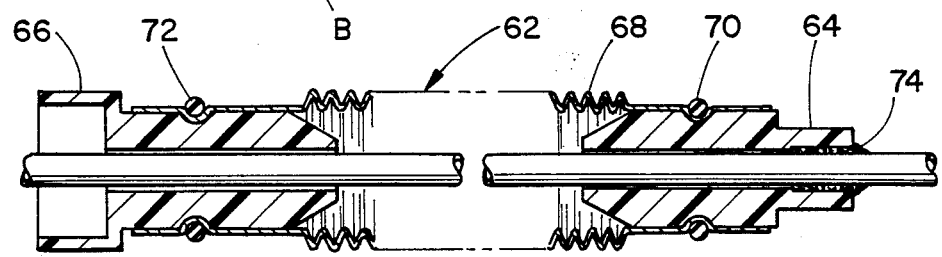

CATHETER PACKAGE

BACKGROUND OF THE INVENTION

This invention relates to protective containers. More specifically, the present invention relates to a catheter protection, preparation and dispensing package.

The invention is particularly applicable to a package designed for holding an intravascular catheter which is adapted for insertion into a vein of a patient, such as a Swan-Ganz brand balloon flotation catheter sold by American Edwards Laboratories, American Hospital Supply Corporation of Evanston, Ill. (Swan-Ganz is a registered trademark). This catheter has a plurality of lumens which allow for injection of various substances into the patient and allows various readings to be made within the vascular system of the patient, such as pressure and temperature readings. It should, however, be appreciated that the package disclosed herein can also be adapted for use in a variety of other catheter packaging environments.

The insertion of vascular catheters, such as balloon flotation catheters, into a patient, requires an absolutely sterile procedure since it is well known that catheter contamination during preparation and insertion of the catheter is a cause of life-threatening infections. Because conventional balloon flotation catheters are long, generally greater than 100 cm for an adult patient, and unwieldy, it is difficult to keep them sterile.

Because of its length and resilient nature, a balloon flotation catheter is cumbersome to control in a limited sterile field after it is removed from its package. Moreover, considerable preparation and testing needs to be done on an exposed catheter prior to its insertion. The present art requires flotation catheters to be exposed to a potentially contaminating environment during preparation, testing and insertion. Previously, a wide area was draped so as to be sterile, along with the operators themselves, so that it made no difference as to how the catheter was handled. Now, while the operators themselves remain sterile, a wide area is not necessarily sterile. Consequently there are many potential sources of contamination during this testing procedure.

Additionally, the procedure requires that a technician be ready at all times in order to assist the physician immediately as needed with the check-out process. While the check-out of the catheter is taking place, of course, the physician has to wait, thereby taking up the physician's time. While all of this is happening, contaminating micro-organisms may enter the sterile field and contaminate the catheter. This could potentially produce life-threatening infections.

Presently, the catheter is disengaged from an ordinary non-compartmentalized package and the terminals for the catheter lumens are attached to their respective tubing connections. Subsequently, some of the catheter ducts are flushed with a saline or heparin solution to avoid clot formation within the lumens or an air embolism in the patient after insertion of the catheter. A sterile sleeve is thereafter pulled over a balloon end of the catheter to provide a protective covering to be used while the catheter is in-dwelling in the patient after the insertion procedure.

A balloon at the distal end of the catheter is sometimes inflated to test for air leaks since catheter insertion is potentially more dangerous if the balloon does not remain inflated. Additionally, an air leak in the balloon may necessitate a second cardiac catheterization with its attendant risk. After the balloon has been tested, the catheter is inserted into an introducer which has previously been placed into a vein of the patient.

The catheter is then passed into a blood vessel of the patient and is advanced through the blood vessel. The inflated balloon draws the catheter tip in the direction of blood flow, and the pressure waveform is used to identify tip location. The catheter is then secured in the desired location and a portion of the catheter extending from the introducer is covered by the protective sleeve in order to maintain this portion in a sterile condition. This length, which may be as long as 40 cm, can be advanced easily into the vein if the catheter has to be moved because it dislodges or migrates.

An improvement over the conventional catheter package is a package having four separately openable lids enclosing various compartments. A smaller compartment contains a proximal end of the catheter including the hubs and allows the connection and flushing of the catheter prior to insertion thereof. A trough covered by two separate lids houses a distal end of the catheter and a pleated glove thereon. A larger compartment contains a main portion of the catheter. A lid for the larger compartment only extends over a relatively small portion of the larger compartment and it is intended that the catheter be pulled out therethrough. The entire assembly is then enclosed in a separate outer bag. This known package is, however, impractical from the standpoint that it is too complex, and therefore expensive to manufacture as well as being difficult to use. It would be desirable to provide a relatively simple compartmented catheter package which would be inexpensive to manufacture and yet provide the advantages of ease of check-out, without the necessity for several people to be occupied with or waiting for this task, ease of removal of the catheter from the package, and assurance of the sterility of an indwelling portion of the catheter until removal.

Accordingly, it has been considered desirable to develop a new and improved catheter preparation and dispensing package which would overcome the foregoing difficulties and others while providing better and more advantageous overall results.

BRIEF SUMMARY OF THE INVENTION

In accordance with the present invention, a new and improved intravascular catheter package is provided for a catheter having adjacent its distal end at least one port, a catheter central portion having a sheath mounted thereon and a proximal end having a pig-tail sheath which is connected to a plurality of inlet tubes.

More particularly in accordance with this aspect of the invention, the catheter package comprises a main housing compartment for housing a distal section of the intravascular catheter with the main housing compartment having an opening for removal of the catheter therethrough. The main housing compartment comprises a first section for housing a distal end portion of the catheter which has the at least one port therein and an absorbent means for absorbing a fluid used to flush the catheter as it flows out through the at least one port. The main housing compartment further includes a second section for housing the catheter central section and the sheath mounted thereon. The second section is located at a higher elevation than the first section to ensure that all of the fluid used to flush the catheter remains in the first section. A means for covering the main housing compartment opening is provided to seal the housing compartment from micro-organisms and particles in the surrounding environment. The means is removable to expose the catheter. A catheter proximal end holding section is provided for holding the proximal end of the catheter. An enclosing means is provided for enclosing both the main housing compartment and the catheter proximal end holding section to seal the catheter from micro-organisms and particles in the surrounding environment.

According to another aspect of the invention, the package further comprises a securing means for securing the plurality of inlet tubes in the catheter proximal end holding section.

According to still another aspect of the invention, the package further comprises a baffle provided in the main housing compartment for separating the first section of the package from the second section thereof.

According to yet another aspect of the invention, the package is used with a catheter having three ports, the first located adjacent the catheter distal end and a second and third port located at a distance therefrom and spaced from each other. The absorbent means is adapted to absorb fluid flowing out of all three of the ports. The absorbent means can be positioned in a recess in a bottom wall of the main housing compartment.

According to yet still another aspect of the invention, the package further comprises a manifold bar to which each of the plurality of inlet tubes is secured in such a manner that an inlet end of each of the plurality of inlet tubes faces away from the main housing compartment. Preferably, the catheter proximal end holding section comprises a holding means for selectively holding the manifold bar so that the manifold bar and the inlet tubes secured thereto can be selectively removed from the catheter proximal end holding section.

In accordance with another aspect of the invention, the means for covering and the closing means are both transparent. Preferably, the enclosing means is gas permeable to allow a sterilizing gas to flow therethrough.

In accordance with still another aspect of the invention, the package further comprises a groove in the main housing compartment first section for housing the portion of the catheter having at least one port.

One advantage of the present invention the provision of a new and improved catheter package which is inexpensive to manufacture and easy to use.

Another advantage of the present invention is the provision of a catheter package having a distal end holding compartment which remains sterile even when a hub or connector end section of the package is exposed to the environment.

Still another advantage of the present invention is the provision of a catheter package which is so fabricated that different sections thereof are disposed at different levels. A lower level contains the distal end portion of the catheter to ensure that only the distal end portion is wetted during flushing.

Yet another advantage of the invention is the provision of a catheter package having a main compartment which is separated by baffles into a set of subsidiary compartments for holding various portions of a distal section of the catheter.

Still yet another advantage of the present invention is the provision of a catheter protector sleeve which is preattached to the catheter. This saves a step for the operator and eliminates the risk of damaging the balloon during passage of the catheter tip through the sleeve hubs.

An additional advantage of the invention is the provision of a holding means for holding a proximal end of the catheter in place.

A further advantage of the invention is the provision of a catheter package which is provided with a manifold for holding the hub ends of the catheter with the manifold constituting a removable end of the package.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangements of parts, preferred embodiments of which will be illustrated in the accompanying drawings which form a part hereof and wherein:

FIG. 2 is a greatly enlarged cross-sectional view along line 2—2 of the catheter package of FIG. 1;

FIG. 3 is an enlarged top plan view illustrating a portion of a catheter proximal end holding section of the catheter package of FIG. 1;

FIG. 4 is an enlarged cross-sectional view through a shield assembly utilized with a catheter stored in the package of FIG. 1;

FIG. 5 is a greatly enlarged cross-sectional view along line 5—5 of the catheter package of FIG. 1;

DETAILED DESCRIPTION OF THE PREFERRED EMBODIMENTS

Figure 1:
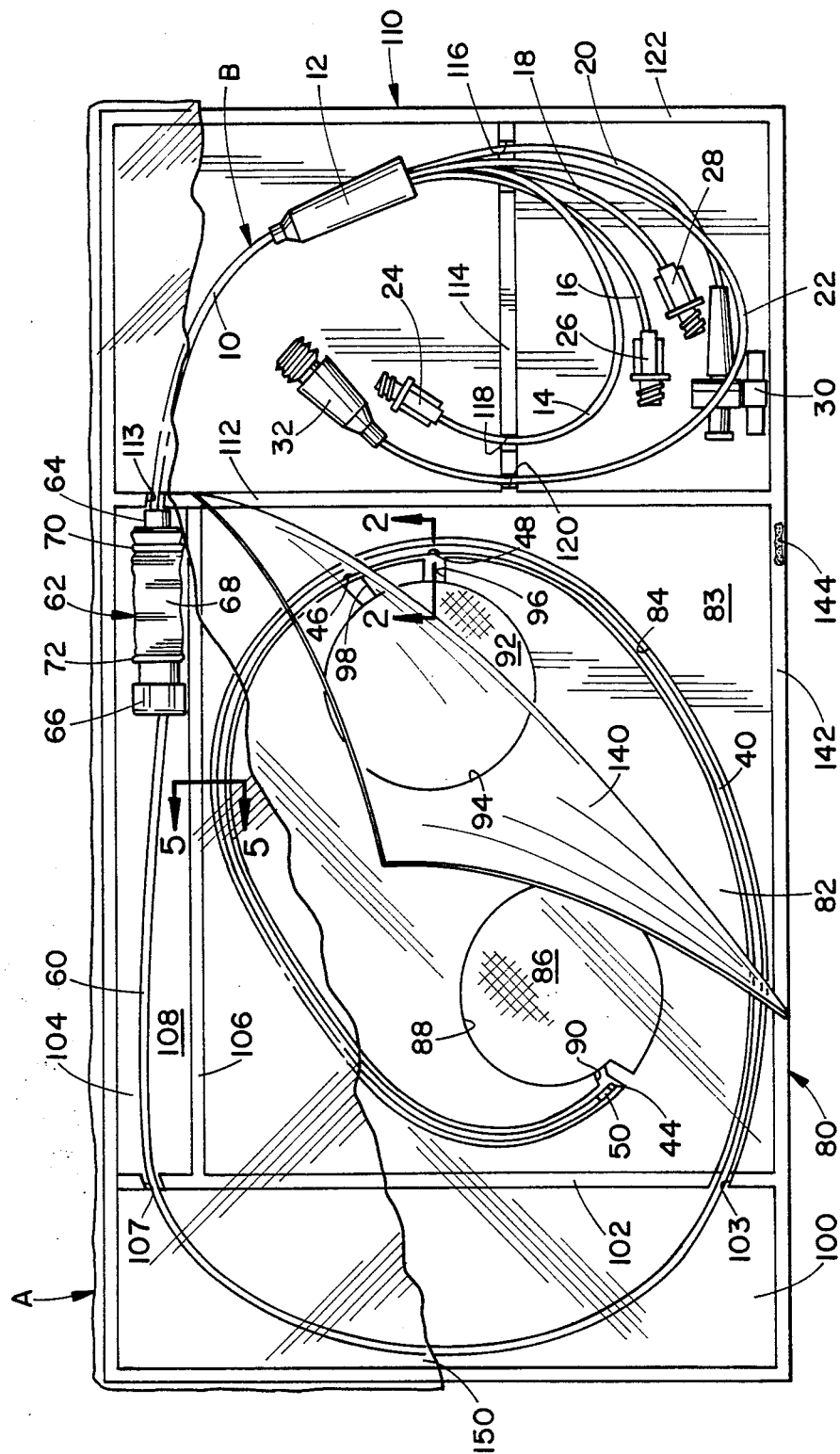
FIG. 1 is a top plan view of a catheter package according to a first preferred embodiment of the present invention.

Referring now to the drawings, wherein the showings are for purposes of illustrating preferred embodiments of the invention only and not for purposes of limiting same, FIG. 1 shows a first preferred embodiment of the subject new package A which is used to hold a catheter B. While the package will be described as being adapted to hold a specific type of catheter, it should be recognized that many other types of catheters could be successfully held in a package constructed according to the invention.

More specifically, the catheter B is a balloon flotation catheter known as a Swan-Ganz brand catheter sold by American Edwards Laboratories, American Hospital Supply Corporation of Evanston, Ill. (Swan-Ganz is a registered trademark). At a proximal end 10, the catheter comprises a pigtail sheath 12 extending from which are a first inlet tube 14, a second inlet tube 16, a third inlet tube 18, and a fourth inlet tube 20. Also extending from the sheath is an electrical conduit 22. Secured on a free end of the first inlet tube 14 is a connector terminal 24. Similarly secured on the free ends of the second and third inlet tubes 16, 18 are similar connector terminals 26 and 28. To a free end of the fourth inlet tube 20 is secured a gas connector terminal 30. An electrical terminal 32 is connected to a free end of the electrical conduit 22.

A distal end 40 of the catheter is provided with a first outlet port 44 which is in fluid communication with the first inlet tube 14 through a fluid line or lumen which is not visible in FIG. 1. Similarly, second and third outlet ports 46, 48 are in fluid communication with a respective one of the second and third inlet tubes 16, 18 through suitable lumens. A balloon section 50 is in fluid communication with the fourth inlet tube 20 through an additional lumen. The lumens can be seen in the enlarged cross section of FIG. 2.

Also provided for the catheter is an intermediate section 60 on which is positioned a shield assembly 62. With reference now also to FIG. 4, the shield assembly comprises a first hub 64 and spaced therefrom a second hub 66. A sheath 68 is secured between the two hubs such that a respective end of the sheath is secured to each hub by suitable O-rings 70, 72, as shown, or by an adhesive. One of the hubs, such as hub 64 is preferably secured such as by an adhesive bead 74 to the intermediate portion 60 of the catheter B. The second hub 66 is adapted to cooperate with a conventional introducer (not illustrated). The second hub can be of the bayonet-type or push-on type as shown or can be of the luer type as known in the art.

The advantage of providing a pre-attached catheter protector sleeve, which can be located at 90 centimeters from the distal end of the catheter if desired, is that this saves a step for the operator and eliminates the risk of damaging the balloon 50 during the passage of the catheter tip through the hubs 64, 66.

With reference now to the package A, it be made from a suitable conventional material such as a plastic. The package includes a main housing compartment 80 which is comprised of a first section 82 having a floor 83 that has a trough or channel 84 extending therein. The trough is adapted to hold the distal end portion 40 of the catheter. A first absorbent means 86, which can be a sponge or an absorbent wad of paper or the like, is provided in a cavity 88 adjacent the first port 44. A suitable channel 90 in the floor 83 communicates the trough 84 with the cavity 88 and enables fluid to flow out of the first port and be absorbed by the absorbent material 86. With reference now also to FIG. 2, a second absorbent means 92 is provided in a cavity 94 adjacent to the second and third ports 46, 48. Suitable respective channels 96, 98 in the floor 83 communicate the trough 84 with the cavity 94 to enable fluid to flow from a respective one of the ports and be absorbed by the material of the absorbent means 92.

The main housing compartment also includes a second section 100 which is separated by a baffle 102 from the first section 82. A slot 103 in the baffle 102 allows the catheter to extend therethrough. A third section 104 is similarly separated by a baffle 106 from the first section 82. A slot 107 in the baffle 102 enables the catheter to extend from the third section 104 into the second section 100. It is noted that the catheter portions which are located in the second and third sections 100, 104 are not shown as being disposed in a trough, but they may be. They could be so disposed in order to define the curve of the catheter.

With reference now to FIG. 5, it can be seen that the catheter B is disposed at a lower elevation in the first section 82, than it is in the third section 104. If desired, a floor 108 of the third section 104 can be located at a higher elevation than the floor 83 of the first section 82 to further alter the elevation of the catheter between the two sections. Preferably, the catheter in the second section 100 is similarly located at a higher elevation than it is the first section 82. In this way, the distal end portion of the catheter B is located at a lower elevation than the rest of the catheter. This is advantageous in order to ensure that only the distal end portion of the catheter is wetted when the lumens of the catheter are flushed.

The package A also includes a catheter proximal end holding section 110. This section is separated by a wall 112 from the main housing compartment 80 and a slot 113 in the wall enables the catheter to extend therethrough. A holding means 114 is provided in this section for holding the various tubes on the proximal end of the catheter. In this regard, it can be seen that the holding means 114 includes a rib in which are provided suitable notches 116, 118, and 120. The first notch 116 is suitably sized so that all of the catheter tubes 14, 16, 18, 20, and 22 can extend therethrough. The second and third notches 118, 120 are suitably sized so that the longest two of the tubes, namely the first inlet tube 14 and the electrical conduit 22 can be held therein. If desired, a suitable exterior wall 122 can surround the proximal end holding section 110. However, such a wall is not necessarily required.

A covering means in the form of a layer 140 covers the main housing compartment 80 and extends over a surrounding wall 142 of the compartment as well as the separating wall 112 between the proximal end holding section 110 and the compartment 80. The covering layer can be secured as by an adhesive strip 144 (only a section of which is shown) to the walls 142, 112 in such a manner that it can be peeled away therefrom when desired. It is noted that no separate covering layer is necessary in this embodiment over the proximal end holding section 110. However, an enclosing means, in the form of a bag 150, is provided for enclosing the entire package.

The bag 150 is preferably gas permeable but impermeable to microorganisms and particles in the surrounding environment. The cover 140 is also preferably gas permeable and impermeable to microorganisms and particles. However, the cover does not have to be gas permeable since a sterilizing which enters the bag 150 can seep into the main housing compartment 80 along slot 113 and travel through the slots 107, 103 in the several baffles to permeate all the sections 82, 100, 104 of the main housing compartment. Preferably, the bag 150 and the cover 140 are transparent to enable the catheter B held therein to be viewed. As is evident from FIG. 1, the cover 140 is adapted to be peeled away from the main housing compartment 80 once the bag 150 has been ripped open.

In use, the entire package is sterilized in the bag 150 with a sterilizing gas. The bag maintains the long term sterility of the entire package once it has been sterilized because it keeps microorganisms and particles out. When a check out of the lumens of the catheter package is desired, the bag 150 is torn open to expose the proximal end of the catheter. The main housing compartment, however, remains covered by the covering sheet 140. The cover is intended to maintain the contents of the main housing compartment in a sterile condition for about an hour in a clean environment.

Once the package has been opened, the terminals 24, 26, 28, 30, 32 can be removed from the package, as shown in FIG. 3, and connected and the lumens flushed before the catheter is needed. Thus, the catheter is ready for use. When a physician needs the catheter, it can be removed from the main housing compartment 80 and inserted immediately into the patient.

It is noted that there is no intention of maintaining an absolute seal for the main housing compartment 80 once the bag 150 has been opened and that air may pass along the catheter in the slot 113 from the proximal end holding section 110 into the main compartment. However, in the absence of gross external physical contamination, the contents of the main housing compartment, i.e. the intermediate portion 60 and distal end 40 of the catheter, which can be approximately the last 100 centimeters of the catheter, can be regarded as remaining sterile for at least an hour after the package is opened and the catheter prepared and flushed with sterile fluid.

It is estimated that the potential time saved per insertion of a catheter held in a package according to the present invention would average approximately two to three minutes or more. Since the total average billing cost for operating room time, professional fees, and technical charges can be approximately $15.00 per minute, it is estimated that the cost savings from the use of the instant catheter package may range from $20.00 to $45.00 per insertion. Considering that there may be as many as 400,000 such catheter insertions annually nationwide, it can be seen that a considerable savings of patient time and money would be afforded by the use of the catheter package disclosed herein.

Moreover, since the patient is subjected to a shorter procedure, the procedure would also be considered inherently safer to some extent. The time during which a catheter is being inserted is difficult for both the patient and the physician. The patient's face is draped and difficult to observe and the physician is gloved and cannot easily administer medications or other treatment. Patients are often a bit uncomfortable and yet are required to remain still. For the vast majority of cases no problems are encountered during catheter insertion. However, substantial problems are encountered occasionally and some of these problems would be avoided simply by decreasing the duration of the procedure.

Additionally, there would be less waste of sterile catheters. In this connection, it is estimated that with conventional packaging, perhaps 1% of catheters are contaminated or damaged during pre-insertion assembly and preparation. It is believed that this loss of catheters would be greatly decreased through use of the inventive catheter package.

Figure 6:
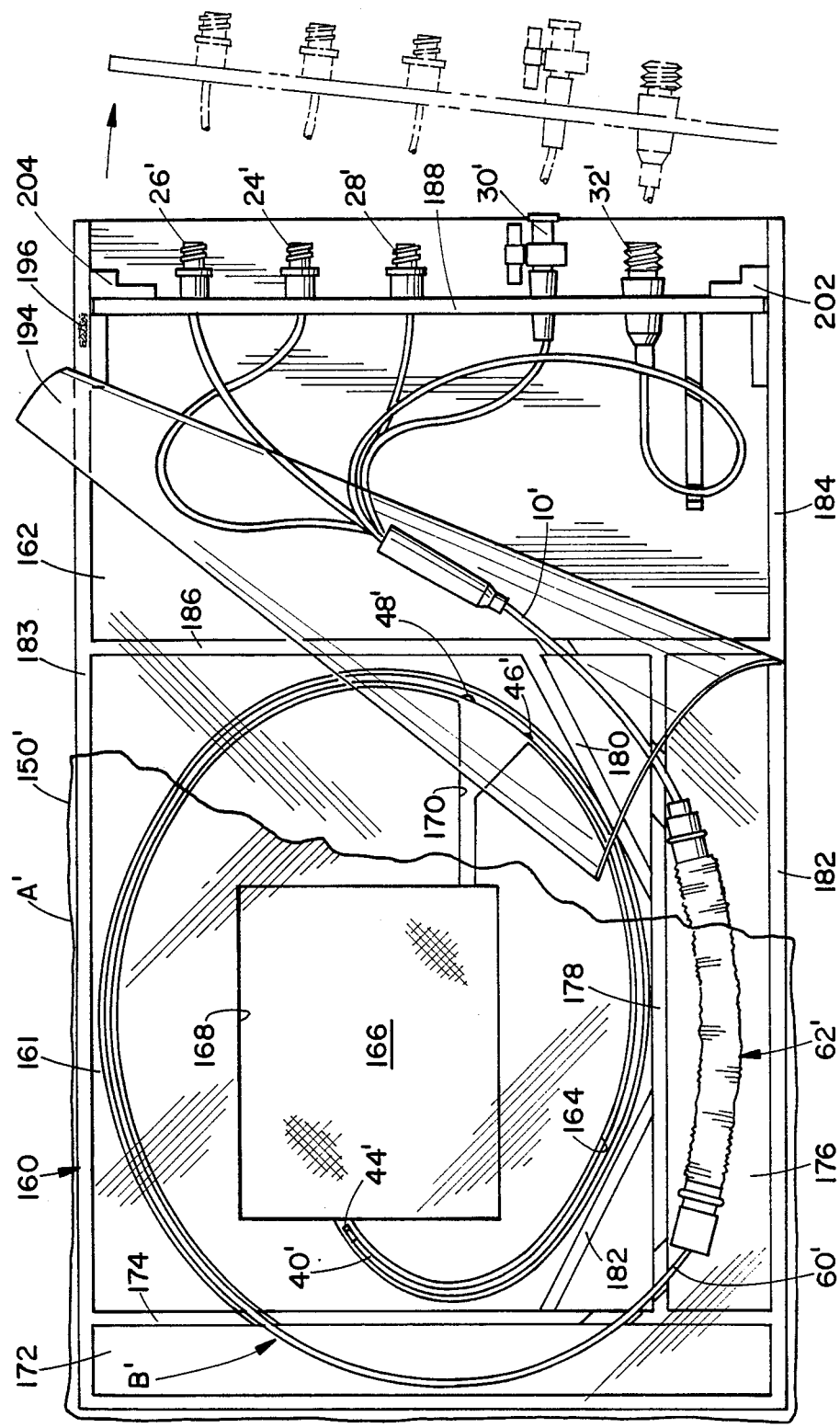
FIG. 6 is a top plan view of a catheter package according to a second preferred embodiment of the present invention; and, FIG. 7 is a top plan view of a third preferred embodiment of a catheter package according to the present invention.

With reference now also to FIG. 6, a second preferred embodiment of the catheter package according to the present invention is there illustrated. For ease of illustration and appreciation of this alternative, like components are identified by like numerals with a primed (') suffix and new components are identified by new numerals.

In this embodiment, the package A' houses a catheter B' which is identical with that disclosed in FIG. 1. Thus, the catheter has a proximal end 10', a distal end 40', and an intermediate portion 60'. The catheter package is provided with a main housing compartment 160 which includes a first section 161 that houses the distal end 40' of the catheter and a proximal end housing compartment 162 for the housing the proximal end 10' of the catheter. The distal end 40' of the catheter is housed in a trough 164. An absorbent material 166, which is located in a cavity 168, is provided for absorbing fluids flushed through the lumens of the catheter and exiting at the various ports 44', 46', and 48' thereof. It is noted that fluid seeps out the first port 44' and communicates with the absorbent material 166 through the trough 164 which extends to the cavity 168. As fluid seeps out the second and third ports 46, 48, it communicates with the absorbent material 166 through a channel 170 which extends between the trough 164 and the cavity 168.

The main housing compartment 160 also includes a second section 172 separated by a baffle 174 from the first section 161 as well as a third section 176. The latter section is similarly separated by suitable baffles 178, 180 and 182 from the first section 161. Suitable slots are provided in the several baffles to allow the catheter to extend therethrough as shown in FIG. 6. The third section 176 holds an intermediate portion 60' of the catheter. This portion has mounted thereon a sheath 62'. In contrast to the sheath illustrated in FIG. 1, the sheath 62' is shown in its extended position as covering most of the catheter intermediate portion 60'.

As in the first embodiment, the catheter in the first section 161 is disposed at a lower elevation than in the second and third sections 172, 176 to ensure that all the excess fluid will be successfully drained into the absorbent material 166. An outer wall 182 encircles three sides of the main compartment 160.

In this embodiment, the proximal end housing compartment 162 includes a pair of side walls 183, 184 as well as a baffle 186 which separates the main compartment 160 from the end compartment 162. A manifold wall 188 defines the fourth wall of the end compartment 162. The manifold wall 188 is so constructed as to house the plurality of terminals 24', 26', 28', 30', and 32' of the catheter B' in a spaced fashion. These terminals are preferably suitably fastened to the manifold wall 188 in a relatively secure manner. In this embodiment, both the main housing compartment 160 and the proximal end housing compartment 162 are covered by a single cover layer 194 which is secured to the container walls 182, 183, 184, 188 by a suitable adhesive strip 196 (only a section of which is illustrated). The entire assembly is then encased by a bag 150'.

In use, once the bag 150' is opened, the several terminals 24', 26', 28', 30', and 32' are accessible to a technician in order to allow the technician to flush the lumens and generally check out the catheter before the catheter needs to be inserted in a patient. When such insertion is imminent, the cover member 194 which, until this time has been secured in place over both the main housing compartment 160 and the end housing compartment 162, can be removed from the package A'. At this point, the manifold wall 188 can be detached from suitably configured first and second end holding sections 202, 204 of the package and removed therefrom as indicated in dashed outlined in FIG. 6. Simultaneously, the rest of the catheter B40 can be removed from the package A'.

Figure 7:
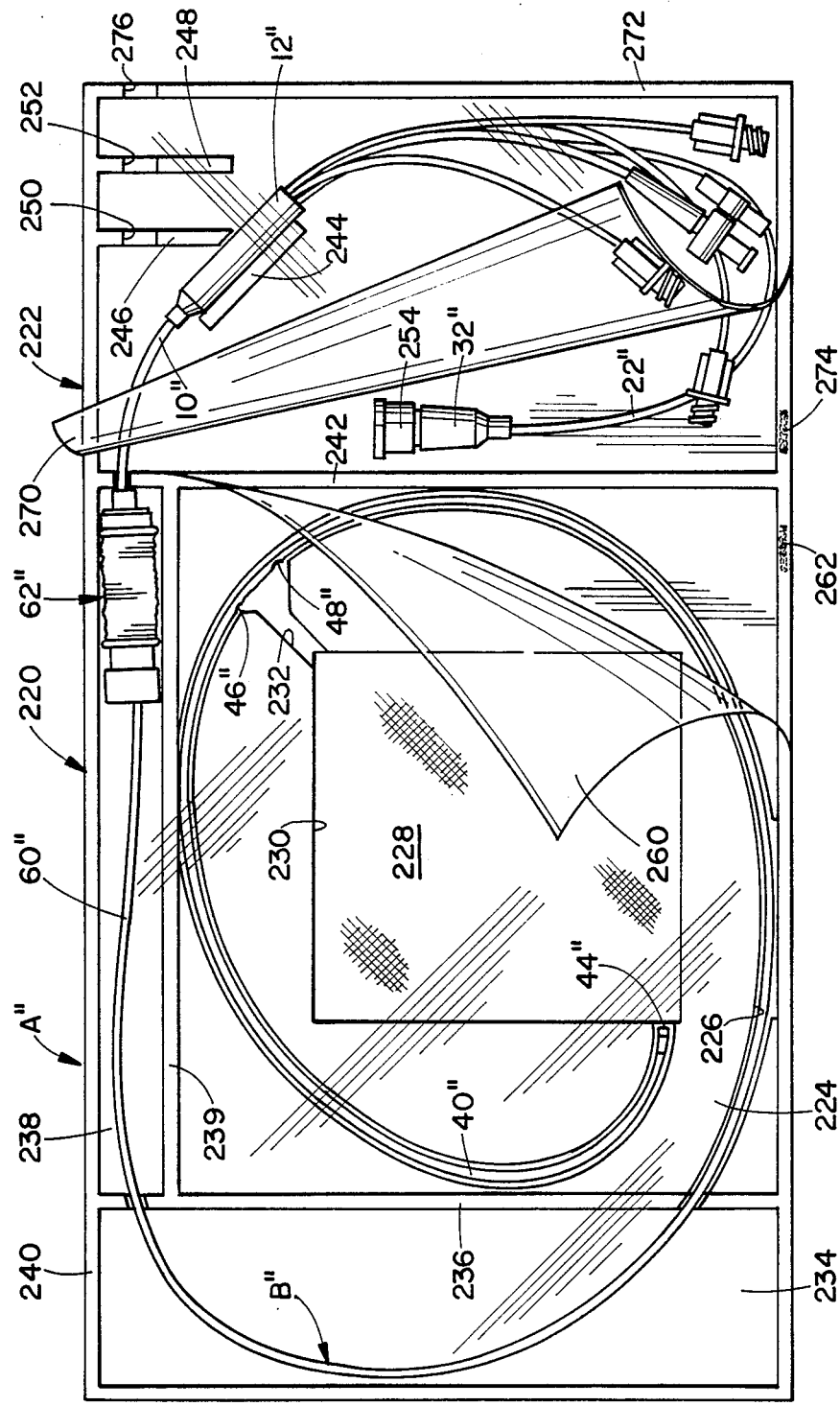

With reference to FIG. 7, a third preferred embodiment of a catheter package according to the present invention is there illustrated. For ease of illustration and appreciation of this alternative, like components are identified by like numerals with a double primed (") suffix and new components are identified by new numerals.

In this Figure, a package A" is provided for housing a catheter B" that comprises a proximal end 10", a distal end 40", and an intermediate portion 60". The package includes the main housing compartment 220 as well as a proximal end housing compartment 222. A first section 224 of the main housing compartment includes a trough 226 in which is looped the distal end 40" of the catheter.

An absorbent material 228 is provided in a cavity 230 for absorbing fluid which is flushed through the lumens of the catheter. As can be seen, the trough 226 communicates with the cavity 230 in order to enable fluids flushed through an end port 44" of the catheter to be absorbed by the material 228. A channel 232 is also provided in order to enable fluids flushed through additional catheter ports 46", 48" to be absorbed by the material 228.

The main housing compartment 220 also includes a second section 234 which is separated from the first section 224 by a suitable baffle 236. A third section 238 of the main housing compartment holds the catheter intermediate section 60", and a sheath 62" mounted thereon, and is separated from the first section 224 by a further baffle 239. As in the previously described embodiments, suitable slots are provided in the several baffles to enable the catheter to extend therethrough. An exterior wall 240 encircles three sides of the main compartment.

The proximal end housing compartment 222 is separated from the main housing compartment 220 by a suitable wall 242. Located in the proximal end housing compartment is a holding means for a pigtail sheath 12" of the catheter. The holding means can comprise first and second suitably configured cooperating rib sections 244, 246 in order to hold the sheath in place while the catheter is in the storage position. Also provided in the proximal end housing compartment 222 is a third rib 248 that is spaced from the second rib. Both the second and third ribs are provided with slots 250, 252 which are used to hold the pigtail sheath 12" when the catheter is being checked and its lumens are being flushed.

The pigtail sheath 12" is connected to a plurality of inlet lines one of which is an electrical conduit 22". Positioned on a free end of the conduit 22" is an electrical terminal 32". In this embodiment a cap 254 is shown as covering the end of the terminal 32". The cap would be removed when the terminal is ready to be connected.

The main housing compartment is enclosed by a cover layer 260 which is secured as by a suitable adhesive strip 262 to the outer wall 240 around the main housing compartment 220 as well as the end wall 242 which separates the main housing compartment from the proximal end housing compartment 222.

In this embodiment, the proximal end housing compartment is similarly covered by a cover layer 270 which is secured to an outer wall 272 that encloses three sides of the proximal end housing compartment as well as over the cover 260 at the end wall 242 between the main housing compartment and the proximal end housing compartment by a suitable adhesive 274. The smaller compartment cover 270 extends over the larger compartment cover 260 and is sealed thereto in a suitable conventional manner so that the cover 270 can be peeled away when it is desired to open the end housing compartment but keep the main housing compartment in its covered state. At such a time, the cover 270 can be peeled away and the catheter proximal end can be accessed in order to remove the several inlet tubes 14", 16", 18", 20" as well as conduit 22" from the compartment for purposes of check out. A suitable slot 276 is provided in the outer wall 272 to enable the several tubes to extend therethrough. The cover 270 extends over the wall 272 so that it covers the slot 276 in the wall in order to ensure that the entire package remains sterile until use. At this time, the pigtail sheath 12" is held in the cooperating slots 250, 252 in the second and third ribs 246, 248 which are provided in the proximal end housing compartment.

If desired, a suitable bag, as is illustrated in FIGS. 1 and 6, can be provided for enclosing the package. In this embodiment, however, the covers 260, 270 are gas permeable to allow a sterilizing gas therethrough, but impermeable to microorganisms and particles. Therefore, a separate bag is not necessarily required.

The invention has been described with reference to preferred embodiments. Obviously, modifications and alterations will occur to others upon a reading and understanding of this specification. It is intended to include all such modifications and alterations insofar as they come within the scope of the appended claims or the equivalents thereof.

Having thus described the preferred embodiments, the invention is now claimed to be:

1. A package for a catheter, the catheter having adjacent its distal end at least a first port, a catheter central portion having a sheath mounted thereon, and a catheter proximal end having a pigtail sheath which is connected to a plurality of inlet tubes, said package comprising:

a main housing compartment for housing a distal section of the catheter, said main housing compartment being substantially horizontally oriented and having a top opening allowing the removal of the catheter therethrough and comprising:

a first section for housing a distal end portion of the catheter including said catheter first port, an absorbent means for absorbing a fluid flowing through said catheter first port, said absorbent means being located in said first section, and a second section located adjacent said first section, for housing the catheter central section and the sheath mounted thereon, wherein said second section supports the catheter at a higher elevation than said first section to ensure that all the excess fluid used to flush the catheter remains in the first section of the main housing compartment;

a means for covering said main housing compartment opening to seal said housing compartment from microorganisms and particles in the surrounding environment but removable to expose the catheter;

a catheter proximal end holding section for holding the proximal end of the catheter; and an enclosing means for enclosing both said main housing compartment and said catheter proximal end holding section to seal the catheter from microorganisms and particles in the surrounding environment.

2. The package of claim 1 further comprising a securing means for securing the plurality of inlet tubes in said catheter proximal end holding section so that they are prevented from moving in relation to said catheter proximal end holding section.

3. The package of claim 1 further comprising a baffle provided in said main housing compartment for separating said first section from said second section.

4. The package of claim 1 wherein the package is adapted to house a catheter having three ports, a first port located at the catheter distal end and second and third ports located at a distance therefrom and spaced from each other, wherein said absorbent means is adapted to absorb fluid flowing out all three of the ports.

5. The package of claim 4 wherein said absorbent means is positioned in a recess provided in a bottom wall of said main housing compartment first section and said catheter ports communicate with said absorbent means through suitable channels disposed in said bottom wall of said main housing compartment first section.

6. The package of claim 1 further comprising a manifold bar to which each of a plurality of inlet tubes of the catheter is secured in such a manner that an inlet end of each of said plurality of inlet tubes faces away from said main housing compartment.

7. The package of claim 6 wherein said catheter proximal end holding section comprises a holding means for holding said manifold bar, and the inlet tubes secured thereto, in such a manner that said manifold bar can be selectively removed from said catheter proximal end holding section.

8. The package of claim 1 wherein said means for covering and said enclosing means are both transparent.

9. The package of claim 1 wherein said enclosing means is gas permeable to allow a sterilizing gas to flow therethrough.

10. The package of claim 1 further comprising a trough provided in a bottom wall of said main housing compartment for holding the catheter.

11. The package of claim 1 further comprising a holding means for holding a pigtail sheath of the catheter when a plurality of inlet tubes extend out of said catheter proximal end holding section.

12. An intravascular catheter preparation and dispensing package, comprising:
 a catheter comprising:
  a distal section having a first port located adjacent the distal end of said catheter and a second port located at a distance from said distal end,
  an intermediate section, and
  a proximal section having a pigtail sheath which is connected to a plurality of inlet tubes, each inlet tube having at its free end a connector terminal, wherein said catheter intermediate section is located between said distal section and said proximal section;
 a housing body which extends horizontally and is open at the top for holding said catheter, said housing body comprising:
  a first section for housing said distal section of said catheter, an absorbent means being provided in said first section for absorbing any fluid which flows through said catheter ports,
  a second section, located adjacent said first section, for housing said catheter intermediate section wherein said second section supports said catheter at a higher elevation than said first section to ensure that all the fluid used to flush said catheter flows into said housing body first section,
  a third section, located adjacent said second section, for housing said catheter proximal section, and,
  a barrier means for separating said first, second, and third sections of said housing body;
 a cover means for covering said housing body first and second sections; and,
 an enclosing means for enclosing said housing body, said catheter held therein, and said cover means.

13. The package of claim 12 further comprising a securing means for securing said plurality of inlet tubes in said housing body third section.

14. The package of claim 12 further comprising a manifold bar to which each of said connector terminals is secured, said manifold bar forming a wall of said housing body.

15. The package of claim 12 further comprising a trough provided in a bottom wall of said housing body first section for holding said catheter distal end.

16. The package of claim 12 further comprising a sheath which encloses a portion of said catheter intermediate section and a securing means for fastening the proximal end of said sheath to said catheter intermediate section.

17. An intravascular catheter package comprising:
 a main housing compartment for housing a distal portion of an intravascular catheter, said main housing compartment having an open top for removal of the catheter therethrough and comprising:
  a first section for housing a distal end portion of the catheter, the distal end being provided with ports,
  a second section, located adjacent said first section, for housing an intermediate portion of the catheter adjacent the distal end, wherein said second section is located at a higher elevation than said first section to ensure that only the distal end portion of the catheter will be wetted by fluid flowing out of the ports;
 a first selectively removable cover which is sealed to said main housing compartment over said open top thereof to seal said main housing compartment from microorganisms and particles in the surrounding environment;
 an end housing compartment for housing a proximal end of the catheter, said end housing compartment having an open top for removal of the catheter therethrough and comprising:
  a first holding means for holding a pigtail sheath of the catheter proximal end in place when the proximal end is held in said end housing compartment,
  a second holding means for holding the pigtail sheath of the catheter proximal end in place when the proximal end is held out of said end housing compartment; and,
 a second selectively removable cover which is sealed to said end housing compartment over the opening thereof to seal said end housing compartment from microorganisms and particles in the surrounding environment.

18. The package of claim 17 further comprising a trough provided in a bottom wall of said main housing compartment first section for holding said catheter distal end.

19. The package of claim 18 further comprising a recess provided in said bottom wall of said main housing compartment first section for holding an absorbent means for absorbing fluid flowing out of said ports.

20. The package of claim 17 further comprising baffles for separating said main housing compartment first and second sections.

* * * * *